United States Patent [19]

Goto et al.

[11] Patent Number: 4,778,620

[45] Date of Patent: Oct. 18, 1988

[54] TOLAN DERIVATIVE AND A LIQUID CRYSTAL MIXTURE CONTAINING THE SAME

[75] Inventors: Yasuyuki Goto; Tetsuya Ogawa, both of Yokohamashi, Japan

[73] Assignee: Chisso Corporation, Japan

[21] Appl. No.: 79,997

[22] Filed: Jul. 31, 1987

[30] Foreign Application Priority Data

Aug. 4, 1986 [JP] Japan .................. 61-182985
Mar. 28, 1987 [JP] Japan .................. 62-75525

[51] Int. Cl.⁴ ............... C09K 19/30; C09K 19/54; C09K 19/06; C07C 13/00
[52] U.S. Cl. ............... 252/299.63; 252/299.5; 252/299.6; 570/128; 585/20
[58] Field of Search ......... 252/299.63, 299.5, 299.6; 350/350 S, 350 R; 568/631, 647; 570/128; 585/20

[56] References Cited

U.S. PATENT DOCUMENTS

| | | | |
|---|---|---|---|
| 3,925,482 | 12/1975 | Jacques | 252/299.6 |
| 4,400,293 | 8/1983 | Romer et al. | 252/299.63 |
| 4,528,114 | 7/1985 | Petrzilka | 252/299.6 |
| 4,583,826 | 4/1986 | Petrzika et al. | 252/299.63 |
| 4,705,870 | 11/1987 | Takatsu et al. | 252/299.63 |
| 4,705,905 | 11/1987 | Tatatsu et al. | 585/25 |
| 4,713,468 | 12/1987 | Takatsu et al. | 252/299.63 |
| 4,726,910 | 2/1988 | Takatsu et al. | 252/299.5 |

FOREIGN PATENT DOCUMENTS

| | | | |
|---|---|---|---|
| 84194 | 7/1983 | European Pat. Off. | 252/299.6 |
| 2234261 | 2/1975 | France | 252/299.6 |
| 2155465 | 9/1985 | United Kingdom | 252/299.63 |

OTHER PUBLICATIONS

Adomenas et al., Advances in LC Research & Appl., vol. 2, pp. 1029–1038, (1980).

*Primary Examiner*—Teddy S. Gron
*Assistant Examiner*—J. E. Thomas
*Attorney, Agent, or Firm*—Leydig, Voit & Mayer

[57] ABSTRACT

A novel tolan derivative compound as a liquid crystal substance having a low viscosity and a good compatibility with existing liquid crystals at low temperatures in addition to a large optical anisotropy value and a high clearing point, and a liquid crystal mixture containing the above compound are provided, which compound is expressed by the formula

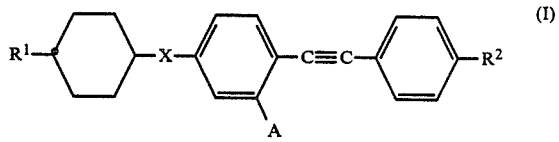

wherein $R^1$ represents an alkyl group of 1 to 10 carbon atoms, $R^2$ represents an alkyl group of 1 to 10 carbon atoms, X represents —$CH_2CH_2$— and A represents an H atom or an F atom.

4 Claims, No Drawings

TOLAN DERIVATIVE AND A LIQUID CRYSTAL MIXTURE CONTAINING THE SAME

BACKGROUND OF THE INVENTION

1. Field of the Invention

This invention relates to a tolan derivative as a novel compound and a liquid crystal mixture containing the same.

2. Description of the Related Art

Display elements having liquid crystals applied thereto make use of the electrooptical effect exhibited by liquid crystal substances, and the display modes thereof include various ones such as those of TN (Twisted Nematic) type, DS (Dynamic Scattering) type, guest-host type, DAP type, etc.

While the properties required for liquid crystal substances used vary depending on these respective modes, the following properties are required in common therewith:

a property that liquid crystal phases are exhibited within as broad a temperature range as possible and a property that the liquid crystal substances are stable to moisture, heat, light, air, etc. At present, however, there is no single compound which satisfies all of such requirements; thus there have been used liquid crystal mixtures obtained by mixing several kinds of liquid crystal compounds or mixing compound(s) similar to liquid crystal compounds with several kinds of liquid crystal compounds.

As to tolan derivatives used as a component of liquid crystal materials, compounds expressed by the following formulas (1) to (3) are disclosed in (1) French patent application laid-open No. 2,141,438, (2) Japanese patent application laid-open No. Sho 60-152427/1985 and (3) Japanese patent application laid-open No. Sho 60-204731/1985, respectively:

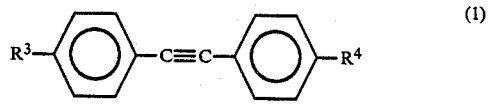
(1)

wherein $R^3$ and $R^4$ each represent an alkyl group or an alkoxy group.

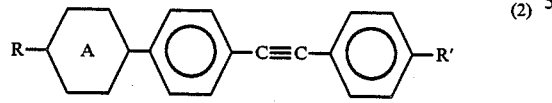
(2)

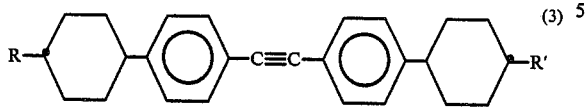
(3)

wherein

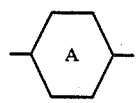

represents

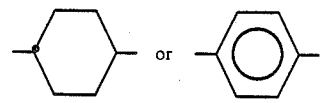

and R and R' each represent a linear chain alkyl group.

These tolan compounds are liquid crystal materials having specific features of a large optical anisotropy value (hereinafter abbreviated to $\Delta n$) and a high clearing point.

SUMMARY OF THE INVENTION

The object of the present invention is to provide a liquid crystal substance having a low viscosity and a good compatibility with existing liquid crystals at low temperatures in addition to the above-mentioned specific features and also to enhance the degree of freeness of choice of liquid crystal materials.

The present invention resides in a tolan derivative compound expressed by the formula

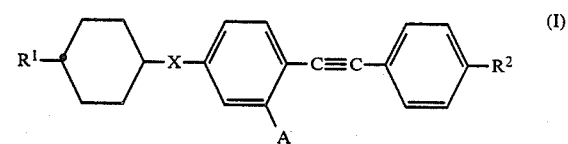
(I)

wherein $R^1$ represents an alkyl group of 1 to 10 carbon atoms, $R^2$ represents an alkyl group or an alkoxy group each of 1 to 10 carbon atoms, X represents —CH$_2$CH$_2$— or a single bond and A represents an H atom or an F atom provided that A represents an F atom in the case where X represents a single bond. The present invention is also directed to a liquid crystal mixture comprising at least two components at least one of which is said tolan derivative compound.

DETAILED DESCRIPTION OF PREFERRED EMBODIMENTS

The embodiments of the present invention include compounds expressed by the following group of formulas:

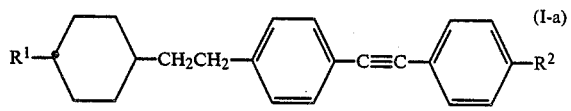
(I-a)

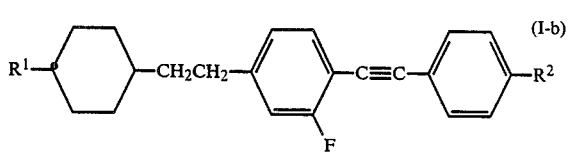
(I-b)

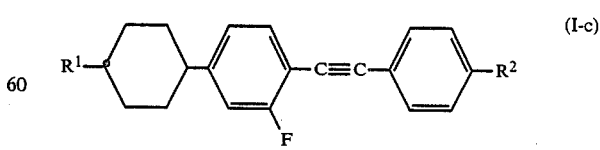
(I-c)

wherein $R^1$ and $R^2$ are as defined above.

These compounds are liquid crystalline compounds having a slightly negative dielectric anisotropy value.

Preferred compounds among those expressed by the formula (I-a) are those wherein $R^1$ represents ethyl, propyl, butyl or pentyl and $R^2$ represents methyl, ethyl, propyl, butyl, pentyl, methoxy, ethoxy, propoxy, butoxy or pentyloxy in the formula (I-a).

For example, 4-(trans-4-propylcyclohexyl)-1-ethyl)-4'-ethyltolan shown in Example 1, described later, is a liquid crystal compound having a large Δn value, a very low viscosity and a braod nematic range and it can constitute a nematic liquid crystal material having various specific features well balanced.

Preferred compounds among those expressed by the formula (I-b) are those wherein $R^1$ represents ethyl, propyl, butyl or pentyl and $R^2$ represents ethyl, propyl, butyl or pentyl in the formula. The tolan derivatives expressed by the formula (1-a) or (1-b) are characterized in that an ethylene group is introduced into a core structure having three six-membered rings bonded linearly. It is presumed that by introducing the ethylene group, a relatively low melting point (i.e. the lower limit temperature of a mesomorphic phase) and a low viscosity have been realized in the compounds of (I-a) and (I-b). Further, it is also presumed that as to be compounds of the formula (I-b), introduction of a fluorine atom as a lateral substituent into the central phenylene ring of the compound of the formula (I-a) may have realized increase in the nematic range and decrease in the smectic range without increasing the viscosity so much as compared to the compound of the formula (I-a). The compound (I-b) is also a nematic liquid crystal having a large Δn value and a low viscosity as in the case of the compound (I-a).

Preferred compounds among those of the formula (I-c) are those wherein $R^1$ or $R^2$ represents ethyl, propyl, butyl or pentyl. Some compounds of the formula (I-c), wherein both $R^1$ and $R^2$ have a long chain alkyl group, have a high viscosity so that such compounds are for practial reasons not particularly preferred. In the compounds of the formula (I-c) the melting point and the clearing point are lowered by a fluorine substitution at a lateral position of the central phenylene ring. Further, as to compounds expressed by the formulas (I-b) and (I-c), a fluorine substitution at a lateral position of the central phenylene ring improves the compatibility of the compound with other liquid crystals at low temperatures.

The compounds of the present invention can be prepared for example according to the following preparation scheme, $R^1$, $R^2$, X and A therein being as defined above:

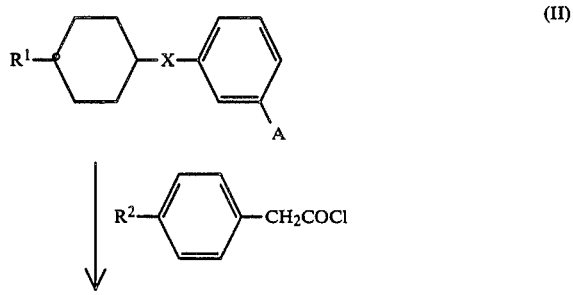

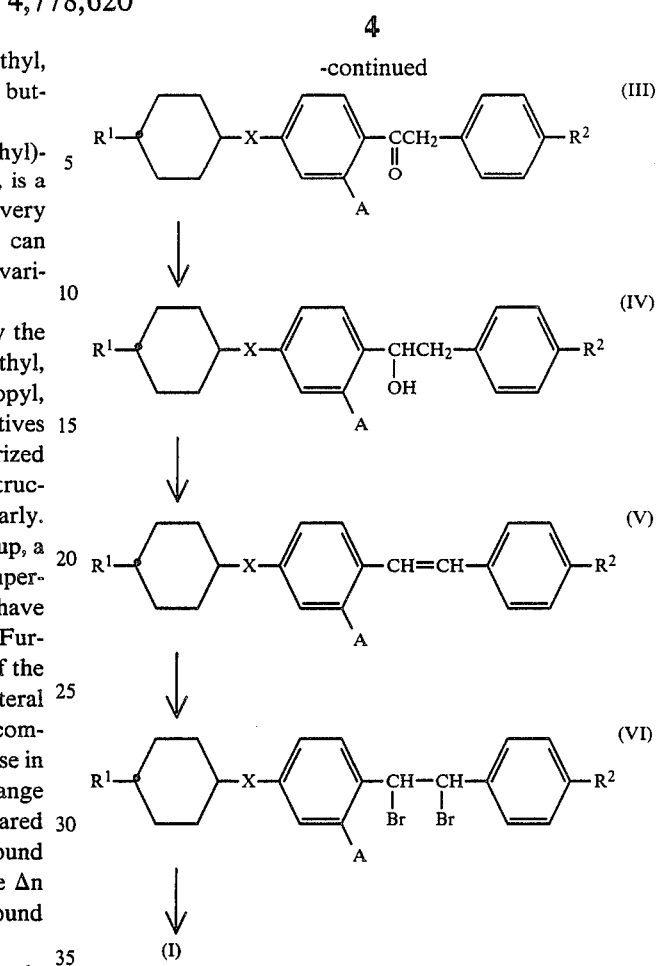

A substituted benzene compound expressed by the formula (II) is first reacted with a 4-substituted-phenylacetyl chloride and anhydrous aluminum chloride in carbon disulfide to obtain a ketone derivative of the formula (III), which is then reacted with a reducing agent such as lithium aluminum hydride in an anhydrous solvent such as ether or tetrahydrofuran to obtain a compound of the formula (IV). Successively this alcohol derivative is subjected to dehydration reaction in the presence of a catalyst mentioned later in an inert organic solvent under atmospheric pressure and at a reflux temperature to obtain an ethylene derivative of the formula (V). As the inert organic solvent, benzene, toluene, chloroform, carbon tetrachloride, methylene chloride, etc. are suitable, and as the catalyst, Lewis acids such as aluminum chloride, tin tetrachloride, titanium tetrachloride, etc., mineral acids such as sulfuric acid, phosphoric acid, etc., toluenesulfonic acid, etc. are usable.

Successively bromine is attached onto the ethylene derivative of the formula (V) in a solvent such as methylene chloride, ethylene chloride, carbon tetrachloride, etc. to obtain a compound of the formula (VI), which is reacted with potassium tertiary-butoxide in tetrahydrofuran solvent, followed by a series of generally known purification procedures of extraction, washing, recyrstallizatuon, etc. to obtain the objective compound of the formula (I). The reactions of the respective steps are known, but the overall reactions are novel.

The substituted benzene of the formula (II) as the starting raw material is obtained by applying a known reaction to an easily commercially available raw material. Namely, a substituted benzene of the formula (II) wherein X represents an ethylene group is obtained by reducing a ketone derivative obtained by a Friedel-Crafts reaction of a trans-4-alkylcyclohexylacetyl chloride with benzene or by coupling reaction of a trans-4-alkylcyclohexylacetyl chloride with bis(3-fluorophenyl)cadmium, while a substituted benzene of the formula (II) wherein X represents a single bond is obtained by subjecting a substituted cyclohexanol obtained by a Grignard reaction of 3-fluorophenylmagnesium bromide with a 4-alkylcyclohexanone, to a dehydration reaction and then a hydrogenation reaction.

Preferred representative examples of liquid crystal compounds used as components of the liquid crystal mixture of the present invention admixture with the compound expressed by the formula (I) are
4-substituted-phenyl 4'-substituted-benzoates,
4-substituted-phenyl 4'-substituted-cyclohexanecarboxylates,
4'-substituted-biphenyl-4-yl 4''-substituted-cyclohexanecarboxylates,
4-substituted-phenyl 4'-(4-substituted-cyclohexanecarbonyloxy)benzoates,
4-substituted-phenyl 4'-(4-substituted-cyclohexyl)benzoates,
4-substituted-cyclohexyl 4'-(4-substituted-cyclohexyl)benzoates,
4,4'-substituted-biphenyls,
4,4'-substituted-phenylcyclohexanes,
4,4''-substituted-terphenyls,
4,4''-substituted-biphenyl-4'-yl-cyclohexanes,
2-(4'-substituted-phenyl)-5-substituted-pyrimidines, etc.

Compounds having lateral substituent(s) of halogen atom(s) or cyano group(s) on the phenylene ring(s) of the above-mentioned compounds may also be used as components of the liquid crystal mixture of the present invention.

As is generally known, in a liquid crystal display element, the product of the cell thickness (d) and the optical anisotropy value ($\Delta n$) of the liquid crystal material employed must be set to a specified value in order to pevent an interference fringe on the cell surface which deteriorates the view of the display. In practice, the value of $\Delta n \times d$ has been set to any one of 0.5, 1.0, 1.6 or 2.2. Since the value of $\Delta n \times d$ is set to definite values as described above, if a liquid crystal material having a large $\Delta n$ value is used, it is possible to reduce the d value. When the d value is reduced, the response time is reduced. Thus, liquid crystal materials having a large $\Delta n$ value are important for preparing a liquid crystal display cell having a high response rate and no interference fringe. Further, in order to reduce the response time, a low viscosity is also necessary.

The compounds corresponding to formula (I) of the present invention are novel nematic liquid crystal compounds having a large $\Delta n$ value (ca. 0.26), a high N-I transition point and further a low viscosity (ca. 16 cp at 20° C.). Thus, when a compound of the formula (I) of the present invention is mixed with various mother liquid crystals, it is possible to prepare a practical liquid crystal material having a low viscosity, a large $\Delta n$ value and a high N-I transition point.

The present invention will be described more concretely by way of examples, but it should not be construed to be limited thereto.

In addition, symbols C-S point, C-N point, S-N point and N-I point in the examples refer to crystalline-smectic transition point, crystalline-nematic transition point, smectic-nematic transition point and nematic-isotropic liquid transition point, respectively.

EXAMPLE 1

4-(Trans-4-propylcyclohexyl-1-ethyl)-4'-ethyltolan

Anhydrous aluminum chloride (27.7 g, 0.21 mol) was added to carbon disulfide (160 cc), followed by adding 4-ethylphenylacetyl chloride (31.7 g, 0.174 mol) under cooling, successively adding trans-4-propylcyclohexylethylbenzene (40 g, 0.174 mol) over about one hour, thereafter agitating the reaction mixture at room temperature for 10 hours, distilling off carbon disulfide, adding the residue to dilute hydrochloric acid aqueous solution, decomposing the resulting aluminum chloride complex with stirring for one hour, extracting the resulting raw crystals with toluene (100 cc), washing with water, drying, distilling off toluene and recrystallizing the remaining solids from ethyl acetate to obtain the following compound (35.3 g):

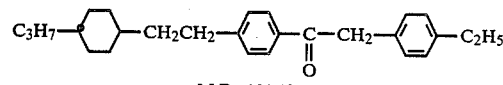

M.P.: 101.8° C.

This compound was dissolved in anhydrous tetrahydrofuran (50 cc), followed by dropwise adding the solution to a solution of lithium aluminum hydride (2.7 g, 0.07 mol) in anhydrous tetrahydrofuran (100 cc), further agitating the mixture at 0° C. for one hour, thereafter adding 20 wt.% sulfuric acid (50 cc) to the reaction mixture to dissolve the inorganic substance, extracting the separated oily substance with toluene (100 cc), washing the separated toluene solution with 10% sodium hydrogen carbonate aqueous solution, further washing with water until the washing water became neutral, drying the resulting toluene solution with anhydrous sodium sulfate, adding p-toluenesulfonic acid (1.8 g), heating the mixture under reflux, removing the formed water to the outside of the system, allowing the resulting material to cool down to room temperature after completion of the reaction, washing the toluene solution with water until the washing water became neutral, drying the toluene solution with anhydrous sodium sulfate, distilling off toluene and recrystallizing the remaining solids from ethyl acetate to obtain the following compound (25 g):

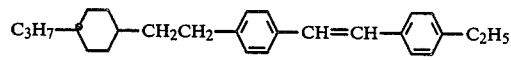

This product exhibited liquid crystal phases and the transition points were as follows: C-S point: 143.9° C., S-N point: 151.3° C. and N-I point: 197.9° C.

This compound was dissolved in methylene chloride (150 cc), followed by dropwise addition of bromine (11.0 g, 0.069 mol) at room temperature and reaction of the mixture for one hour, thereafter distilling off methylene chloride and recrystallizing the remaining solids from n-heptane to obtain the following compound (24.5 g):

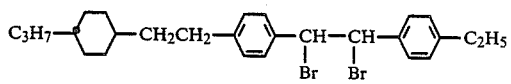

-continued

M.P.: 204.5° C.

This compound was then dissolved in anhydrous tetrahydrofuran (100 cc), followed by adding potassium tertiary-butoxide (22.5 g, 0.20 mol), agitating the mixture at 40° C. for 2 hours, thereafter adding water (200 cc) to the reaction mixture, extracting the separated raw crystals with toluene (100 cc), washing with water, drying, distilling off toluene and recrystallizing the remaining solids from ethyl acetate to obtain the following compound (15.0 g):

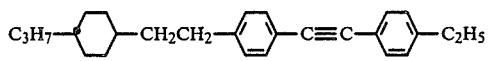

This compound exhibited liquid crystal phases and the transition points were as follows: C-S point: 68.7° C., S-N point: 74.1° C. and N-I point: 161.8° C.

EXAMPLES 2 TO 16

Tolan derivatives obtained in the same manner as in Example 1 and their phase transition points are shown in Table 1 together with the results of Example 1.

TABLE 1

$R^1$—⬡—CH$_2$CH$_2$—⬡—C≡C—⬡—$R^2$

| | | | Phase transition point (°C.) | | |
|---|---|---|---|---|---|
| Example | $R^1$ | $R^2$ | C-S point or C-N point | S-N point | N-I point |
| 1 | n-C$_3$H$_7$ | C$_2$H$_5$ | 68.7 | 74.1 | 161.8 |
| 2 | C$_2$H$_5$ | CH$_3$ | 84.3 | | 144.1 |
| 3 | C$_2$H$_5$ | C$_2$H$_5$ | 69.4 | | 141.2 |
| 4 | C$_2$H$_5$ | n-C$_3$H$_7$ | 66.1 | | 149.2 |
| 5 | C$_2$H$_5$ | n-C$_4$H$_9$ | 59.1 | 62.3 | 137.4 |
| 6 | n-C$_3$H$_7$ | CH$_3$ | 83.6 | | 169.1 |
| 7 | n-C$_3$H$_7$ | n-C$_3$H$_7$ | 67.1 | 77.6 | 166.6 |
| 8 | n-C$_3$H$_7$ | n-C$_4$H$_9$ | 36.4 | 90.0 | 158.8 |
| 9 | n-C$_4$H$_9$ | CH$_3$ | 85.6 | (77.8) | 162.3 |
| 10 | n-C$_4$H$_9$ | C$_2$H$_5$ | 69.5 | 92.7 | 155.7 |
| 11 | n-C$_4$H$_9$ | n-C$_3$H$_7$ | 65.6 | 94.2 | 161.6 |
| 12 | n-C$_4$H$_9$ | n-C$_4$H$_9$ | 59.8 | 103.1 | 152.5 |
| 13 | n-C$_5$H$_{11}$ | CH$_3$ | 91.7 | (85.6) | 165.3 |
| 14 | n-C$_5$H$_{11}$ | C$_2$H$_5$ | 81.5 | 100.4 | 158.0 |
| 15 | n-C$_5$H$_{11}$ | n-C$_3$H$_7$ | 67.9 | 112.1 | 165.4 |
| 16 | n-C$_5$H$_{11}$ | n-C$_4$H$_9$ | 55.2 | 119.9 | 156.3 |

In Table 1 and the succeeding Tables 2 and 3, the symbol ( ) indicates a monotropic transition point.

EXAMPLES 17 TO 25

Compounds shown in Table 2 were obtained from 3-(trans-4-alkylcyclohexylethyl)fluorobenzenes and 4-substituted-phenylacetyl chlorides in the same manner as in Example 1.

TABLE 2

$R^1$—⬡—CH$_2$CH$_2$—⬡(F)—C≡C—⬡—$R^2$

| | | | Phase transition point (°C.) | | |
|---|---|---|---|---|---|
| Example | $R^1$ | $R^2$ | C-S point or C-N point | S-N point | N-I point |
| 17 | C$_2$H$_5$ | n-C$_3$H$_7$ | 36.0 | | 135.2 |
| 18 | C$_2$H$_5$ | n-C$_4$H$_9$ | 26.1 | | 126.5 |
| 19 | n-C$_3$H$_7$ | CH$_3$ | 73.2 | | 158.3 |
| 20 | n-C$_3$H$_7$ | C$_2$H$_5$ | 50.8 | | 149.8 |
| 21 | n-C$_3$H$_7$ | n-C$_3$H$_7$ | 50.2 | | 155.5 |
| 22 | n-C$_3$H$_7$ | n-C$_4$H$_9$ | 42.0 | | 148.6 |
| 23 | n-C$_4$H$_9$ | C$_2$H$_5$ | 58.3 | | 147.8 |
| 24 | n-C$_4$H$_9$ | n-C$_3$H$_7$ | 56.5 | (43.5) | 155.1 |
| 25 | n-C$_4$H$_9$ | n-C$_4$H$_9$ | 50.4 | 71.8 | 147.1 |

EXAMPLES 26 TO 32

Compounds shown in Table 3 were obtained from 3-(trans-4-alkylcyclohexyl)fluorobenzenes and 4-substituted-phenylacetyl chlorides in the same manner as in Example 1.

TABLE 3

$R^1$—⬡—⬡(F)—C≡C—⬡—$R^2$

| | | | Phase transition point (°C.) | |
|---|---|---|---|---|
| Example | $R^1$ | $R^2$ | S-N point | N-I point |
| 26 | n-C$_3$H$_7$ | CH$_3$ | 103.5 | 198.0 |
| 27 | n-C$_3$H$_7$ | C$_2$H$_5$ | 78.3 | 191.0 |
| 28 | n-C$_3$H$_7$ | n-C$_3$H$_7$ | 79.1 | 199.3 |
| 29 | n-C$_3$H$_7$ | n-C$_4$H$_9$ | 50.5 | 187.7 |
| 30 | C$_2$H$_5$ | C$_2$H$_5$ | 50.6 | 166.9 |
| 31 | C$_2$H$_5$ | n-C$_3$H$_7$ | 49.8 | 175.8 |
| 32 | C$_2$H$_5$ | n-C$_4$H$_9$ | 49.3 | 162.1 |

EXAMPLE 33

A liquid crystal mixture A consisting of

| trans-4-propyl-(4-cyanophenyl)cyclohexane | 30% by weight, |
| trans-4-pentyl-(4-cyanophenyl)cyclohexane | 40% by weight, |
| trans-4-heptyl-(4-cyanophenyl)cyclohexane | 30% by weight | has a N-I point of 52.1° C., a viscosity of 20° C. of 22.4 cp and an optical anisotropy value Δn of 0.119.

When 4-(trans-4-propylcyclohexyl-1-ethyl)-4'-ethyltolan (15 parts by weight) as a compound of the present invention shown in Example 1 was added to the liquid crystal mixture A (85 parts by weight), the N-I point of the resulting liquid crystal mixture rose to 68.0° C., the viscosity at 20° C. thereof lowered to 19.0 cp and the optical anisotropy value Δn thereof rose to 0.142.

Further, even when this liquid crystal mixture was allowed to stand at −30° C. for 30 days, no deposition of crystal occurred.

EXAMPLE 34

When 2-fluoro-4-(trans-4-propylcyclohexyl-1-ethyl)-4'-ethyltolan (15 parts by weight) as a compound of the present invention shown in Example 20 was added to the liquid crystal mixture A (85 parts by weight) used in Example 33, the N-I point of the resulting liquid crystal mixture rose to 65.0° C., the visocisty at 20° C. thereof lowered to 20.8 cp and the optical anisotropy value Δn rose to 0.140.

Further, even when this liquid crystal mixture was allowed to stand at −30° C. for 30 days, no deposition of crystal occurred.

EXAMPLE 35

When 2-fluoro-4-(trans-4-propylcyclohexyl)-4'-ethyltolan (15 parts by weight) as a compound of the present invention shown in Example 27 was added to the liquid crystal mixture A (85 parts by weight) used in Example 33, the N-I point of the resulting liquid crystal mixture rose to 66.7° C., the viscosity at 20° C. lowered to 21.0 cp and the optical anisotropy value Δn rose to 0.140.

Further, even when this liquid crystal mixture was allowed to stand at −30° C. for 30 days, no deposition of crystal occurred.

It can be seen from these Examples that the compound of the formula (I) of the present invention can raise the N-I point of the mother liquid crystals up to a practically sufficient value, can raise the Δn thereof and yet can reduce the viscosity thereof and also is a liquid crystal material having a superior compatibility at low temperatures.

COMPARATIVE EXAMPLE 1

When 4-(trans-4-propylcyclohexyl)-4'-ethyltolan (15 parts by weight) as one of tolan derivatives shown in the formula (2) as a prior art was added to the liquid crystal mixture A (85 parts by weight) used in Example 33, the N-I point of the resulting liquid crystal mixture rose to 68.3° C., the viscosity at 20° C. thereof was 22.8 cp and the optical anisotropy value thereof rose to 0.141, but when the mixture was allowed to stand at −30° C., deposition of crystal occurred in only one day.

COMPARATIVE EXAMPLE 2

When 4-(4-propylphenyl)-4'-ethyltolan (15 parts by weight) as one of tolan derivatives shown in the formula (2) as a prior art was added to the liquid crystal mixture A (85 parts by weight) used in Example 33, the N-I point of the resulting liquid crystal mixture rose to 70.3° C. and the Δn thereof rose to 0.145, but the viscosity at 20° C. thereof also rose to 28.0 cp. When this liquid crystal mixture was allowed to stand at −30° C., deposition of crystal occurred in only 5 hours.

What we claim is:

1. A tolan derivative compound expressed by the formula

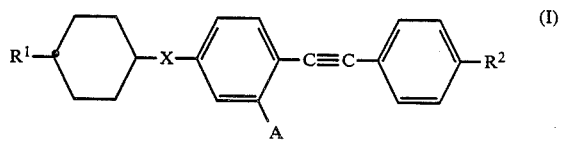

wherein $R^1$ represents an alkyl group of 1 to 10 carbon atoms, $R^2$ represents an alkyl group of 1 to 10 carbon atoms, X represents —$CH_2CH_2$— and A represents an H atom or an F atom.

2. A tolan derivative compound according to claim 1 wherein A represents H.

3. A tolan derivative compound according to claim 1 wherein said X represents —$CH_2CH_2$— and said A represents F.

4. A liquid crystal mixture comprising at least two components at least one of which is a tolan derivative compound expressed by the formula

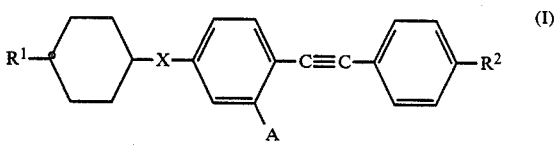

wherein $R^1$ represents an alkyl group of 1 to 10 carbon atoms, $R^2$ represents an alkyl group of 1 to 10 carbon atoms, X represents —$CH_2CH_2$— and A represents an H atom or an F atom.

* * * * *